United States Patent
McConnell et al.

(10) Patent No.: US 12,063,949 B2
(45) Date of Patent: *Aug. 20, 2024

(54) MIXTURE OF HMOs

(71) Applicant: GLYCOM A/S, Hørsholm (DK)

(72) Inventors: Bruce McConnell, La Tour de Peilz (CH); Louise Kristine Vignæs, Copenhagen (DK)

(73) Assignee: GLYCOM A/S, Hørsholm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/929,905

(22) Filed: Sep. 6, 2022

(65) Prior Publication Data

US 2023/0000127 A1 Jan. 5, 2023

Related U.S. Application Data

(63) Continuation of application No. 16/062,598, filed as application No. PCT/IB2016/057675 on Dec. 15, 2016, now Pat. No. 11,432,578.

(30) Foreign Application Priority Data

Dec. 15, 2015 (EP) .................................... 15200067
Feb. 3, 2016 (EP) .................................... 16154144

(51) Int. Cl.
| | | |
|---|---|---|
| A23L 33/00 | (2016.01) | |
| A23L 33/135 | (2016.01) | |
| A61K 31/702 | (2006.01) | |
| A61P 31/04 | (2006.01) | |
| A61P 31/12 | (2006.01) | |
| A23L 33/12 | (2016.01) | |
| A23L 33/19 | (2016.01) | |
| A23L 33/195 | (2016.01) | |

(52) U.S. Cl.
CPC ............. *A23L 33/40* (2016.08); *A23L 33/135* (2016.08); *A61K 31/702* (2013.01); *A61P 31/04* (2018.01); *A61P 31/12* (2018.01); *A23L 33/12* (2016.08); *A23L 33/19* (2016.08); *A23L 33/195* (2016.08); *Y02A 50/30* (2018.01)

(58) Field of Classification Search
CPC ........ A23L 33/40; A23L 33/135; A23L 33/19; A23L 33/195; A61K 31/702; A61K 31/12; A61K 31/04; A61K 2300/00
USPC ............................................. 424/535; 514/54
See application file for complete search history.

(56) References Cited

U.S. PATENT DOCUMENTS

| | | |
|---|---|---|
| 8,586,332 B2 | 11/2013 | Samain et al. |
| 10,471,084 B2 | 11/2019 | Mcconnel |
| 11,040,049 B2 * | 6/2021 | McConnell ........ A61K 31/7016 |
| 11,040,050 B2 * | 6/2021 | Vigsnæs ............ A61K 31/7016 |
| 11,278,558 B2 * | 3/2022 | Vigsnæs .................. A61P 1/00 |
| 11,696,921 B2 * | 7/2023 | Vigsnæs .................. A61P 3/04 514/61 |
| 2012/0171165 A1 * | 7/2012 | Buck ........................ A61P 1/00 514/23 |

FOREIGN PATENT DOCUMENTS

| | | |
|---|---|---|
| EP | 0577580 A2 | 1/1994 |
| EP | 2465509 A1 | 6/2012 |
| WO | 0104341 A1 | 1/2001 |
| WO | 2007101862 A1 | 9/2007 |
| WO | 2010115934 A1 | 10/2010 |
| WO | 2010115935 A1 | 10/2010 |
| WO | 2011100979 A1 | 8/2011 |
| WO | 2011100980 A1 | 8/2011 |
| WO | 2012076323 A1 | 6/2012 |
| WO | 2012155916 A1 | 11/2012 |
| WO | 2012156898 A1 | 11/2012 |
| WO | 2012159897 A1 | 11/2012 |
| WO | 2013044928 A1 | 4/2013 |
| WO | 2013057061 A1 | 4/2013 |
| WO | 2013091660 A1 | 6/2013 |
| WO | 2013139344 A1 | 9/2013 |
| WO | 2013185780 A1 | 12/2013 |
| WO | 2015032412 A1 | 3/2015 |
| WO | 2015071402 A1 | 5/2015 |
| WO | 2017103019 A1 | 6/2017 |
| WO | 2018206434 A1 | 11/2018 |

OTHER PUBLICATIONS

Klindworth, A. et al., "Evaluation of general 16S ribosomal RNA gene PCR primers for classical and next-generation sequencing-based diversity studies," Nucleic Acids Research, 2013, vol. 41(1), 11 pages.

(Continued)

*Primary Examiner* — Ganapathy Krishnan
(74) *Attorney, Agent, or Firm* — Neal, Gerber & Eisenberg LLP

(57) ABSTRACT

A synthetic mixture of human milk oligosaccharides (HMOs) consisting essentially of lacto-N-neotetraose (LNnT), lacto-N-tetraose (LNT), 2'-fucosyllactose (2'FL), 3'-O-sialyllactose (3'-SL), 6'-O-sialyllactose (6'-SL) either difucosyllactose (DFL) or 3-fucosyllactose (3-FL), preferably DFL, and optionally lactose. Said synthetic composition is useful for: treating or preventing viral and/or bacterial infection in a non-infant human; modulating the microbiota of a non-infant human; and/or improving the cognitive function of a non-infant human and as a pharmaceutical or nutritional composition.

20 Claims, No Drawings

(56) References Cited

OTHER PUBLICATIONS

Urashima, T. et al. (2011) Nutrition and Diet Research Progress: Milk Oligosaccharides. New York: Nova Science Publishers, Inc. 92 pages.
Ringel-Kulka, T., et al., "Intestinal Microbiota in Healthy U.S. Young Children and Adults—A High Throughput Microarray Analysis," PLOS ONE, 2013, vol. 8(5), e64315.
Natividad, J.M., et al., "Human Milk Oligosaccharides and Lactose Differentially Affect Infant Gut Microbiota and Intestinal Barrier In Vitro," Nutrients, 2022, vol. 14, pp. 1-23.
Odiase, E., et al., "The Gut Microbiota Differ in Exclusively Breastfed and Formula-Fed United States Infants and are Associated with Growth Status," The Journal of Nutrition, 2023, vol. 153, pp. 2612-2621.

* cited by examiner

MIXTURE OF HMOs

CROSS-REFERENCE TO RELATED APPLICATION

This application is a continuation of U.S. patent application Ser. No. 16/062,598, filed on Jun. 14, 2018, which is a national stage entry pursuant to 35 U.S.C. § 371 of International Application No. PCT/IB2016/057675, filed on Dec. 15, 2016, which claims priority to European Patent Application No. 15200067.5, filed Dec. 15, 2015, and European Patent Application No. 16154144.6, filed Feb. 3, 2016, the contents of all of which are fully incorporated herein by reference.

FIELD OF THE INVENTION

The present invention relates to synthetic mixtures of human milk oligosaccharides ("HMOs"), particularly of LNnT, LNT, 2'-FL, 3'-SL, 6'-SL and either DFL or 3-FL and applications of the mixtures in human health.

BACKGROUND OF THE INVENTION

HMOs have become the subject of much interest in recent years due to their roles in numerous biological processes occurring in the human organism. Mammalian milk contains at least 130 of these complex oligosaccharides (Urashima et al, Milk Oligosaccharides, Nova Biomedical Books, New York, 2011, ISBN: 978-1-61122-831-1).

Previously, the only source of HMOs had been mammalian milk which contains mostly water, together with 55-70 g/l lactose, 24-59 g/l lipids, ca. 13 g/l proteins, 5-15 g/l HMOs and ca. 1.5 g/l minerals.

However, several processes for synthesizing HMOs have been developed in recent years due to their roles in numerous human biological processes. In this regard, processes have been developed for producing HMOs by microbial fermentations, enzymatic processes, chemical syntheses, or combinations of these technologies. For example, by chemical processes, Galp$\beta$1-4GlcNAcp$\beta$1-3Galp$\beta$1-4Glc or lacto-N-neotetraose ("LNnT") can be made as described in WO 2011/100980 and WO 2013/044928; Galp$\beta$1-3GlcNAcp$\beta$1-3Galp$\beta$1-4Glc or lacto-N-tetraose ("LNT") can be synthesized as described in WO 2012/155916 and WO 2013/044928; 6'-O-sialyllactose ("6'-SL) can be synthesized as described in WO 2011/100979; a mixture of LNT and LNnT can be made as described in WO 2013/091660; 2'-O-fucosyllactose ("2'-FL") can be made as described in WO 2010/115934 and WO 2010/115935; 3-fucosyllactose ("3-FL") can be made as described in WO 2013/139344; and 6'-SL can be made as described in WO 2010/100979. As examples of biotechnological processes, WO 01/04341 and WO 2007/101862 describe how to make core human milk oligosaccharides optionally substituted by fucose or sialic acid, including LNnT, 6'-SL and 3'-O-sialyllactose ("3'-SL") using genetically modified E. coli; and WO 2015/032412 describes making 2'-FL and difucosyllactose or Fuc($\alpha$1-2)Gal($\beta$1-4)[Fuc($\alpha$1-3)]Glc ("DFL") using genetically modified E. coli. As an example of enzymatic processes, sialylated oligosaccharides can be made as described in EP-A-577580.

Efforts have also been made to develop processes for synthesizing enzymatically mixtures of HMO oligosaccharides, without having to synthesize all of the component oligosaccharides of the mixture as described in WO 2012/156897 and WO 2012/156898. Such processes have provided reaction mixtures containing a plurality of different oligosaccharides.

Evidence is accumulating that the resident community of microbes, called the microbiota, in the human digestive tract plays a major role in health and disease. When the composition of the intestinal microbiota is thrown off balance, the human host can suffer consequences. Recent research has implicated intestinal microbiota imbalances in individual disorders as diverse as cancer, obesity, inflammatory bowel disease, psoriasis, asthma, and possibly even autism. Individual non-digestible fibres, including HMOs, are believed to beneficially modulate the microbiota, and they are of increasing interest for treating one or more of such disorders. However, many digestible fibres non-specifically modulate the microbiota while others are not able to provide sufficiently broad, but specific, modulation.

Therefore, there has been a need to specifically modulate the microbiota, so as to address individual disorders in different ways and also to address simultaneously multiple disorders. In particular, there has been a need for a composition that can be used for, inter alia, treating and/or preventing bacterial and viral infections, particularly in the intestinal and respiratory tracts, improving cognitive function and/or increasing the efficacy of anticancer agents against tumors.

SUMMARY OF THE INVENTION

A first aspect of this invention relates to a synthetic mixture of HMOs consisting essentially of LNnT, LNT, 2'-FL, 3'-SL, 6'-SL and either DFL or 3-FL, preferably DFL. This mixture can optionally include lactose. The mixture of HMOs preferably consists essentially of:
i. about 55 wt % to about 75 wt % of 2'-FL, more preferably about 60 wt % to about 70 Wt % of 2'-FL;
ii. about 2 wt % to about 10 wt % of LNnT, more preferably about 3 wt % to about 7 wt % of LNnT;
iii. about 10 wt % to about 20 wt % of LNT, more preferably about 12 wt % to about 18 wt % of LNT;
iv. about 1 wt % to about 15 wt % of DFL or 3-FL, more preferably about 1 wt % to about 10 wt %, even more preferably about 2 wt % to about 10 wt % of DFL or 3-FL such as e.g. about 2 wt % to about 8 wt %;
v. about 1 wt % to about 10 wt % of 3'-SL, more preferably about 2 wt % to about 8 wt % of 3'-SL; and
vi. about 1 wt % to about 15 wt % of 6'-SL, preferably about 5 wt % to about 15 wt % of 6'-SL, more preferably about 7 wt % to about 13 wt % of 6'-SL.

A second aspect of the invention relates to a nutritional or pharmaceutical composition comprising a synthetic mixture of HMOs according to the first aspect of the invention.

A third aspect of this invention relates to a synthetic mixture of HMOs or a composition comprising a synthetic mixture of HMOs for use in: i) preventing and/or treating viral and/or bacterial infections in a non-infant human; ii) specifically modulating the indigenous microbiota of a non-infant human; and/or iii) improving the cognitive function of a non-infant human. The synthetic mixture of HMOs consists essentially of LNnT, LNT, 2'-FL, 3'-SL, 6'-SL, either DFL or 3-FL, preferably DFL, and optionally lactose, as described above. The synthetic HMO mixture or the nutritional or pharmaceutical composition comprising it contains a plurality of different HMOs with novel combinations of properties and biological activities. The composition is especially useful against viral and bacterial, intestinal infections through specific modulation of the intestinal microbiota by an increase in *Bifidobacterium*, modulation of intestinal binding of viruses and pathogenic bacteria to intestinal epithelial cells, and improvement of intestinal barrier function. The composition is also especially useful against viral and bacterial, respiratory tract infections by inhibiting pathogen binding to human epithelial cells.

A fourth aspect of this invention relates to a method of modulating the indigenous microbiota of a non-infant human to increase the abundance of *Bifidobacterium* in order to increase the efficacy of anticancer agents against tumors in a non-infant human patient. The method involves administering to the non-infant human a synthetic mixture of HMOs according to the first aspect of this invention or a nutritional or pharmaceutical composition according to the second aspect of this invention, as described above. *Bifidobacterium* can act as an immune booster, hence the increase in its abundance can strengthen a cancer patient's response to an anticancer agent. This property makes the mixture suitable as an aid in cancer therapy.

A fifth aspect of this invention relates to a method of modulating the indigenous intestinal microbiota of a non-infant human to increase *Bifidobacterium* and/or *Barnesiella* abundance and also to reduce the abundance of *Ruminococcus gnavus*. The method involves administering to the non-infant human a synthetic mixture of HMOs according to the first aspect of this invention or a nutritional or pharmaceutical composition according to the second aspect of this invention, as described above. The increased *Bifidobacterium* and/or *Barnesiella* abundance and reduced abundance of *Ruminococcus gnavus* render the non-infant human's intestinal milieu less prone to inflammation and provide improved intestinal barrier function. These effects can prevent and/or treat conditions such as inflammatory bowel disease, irritable bowel syndrome, and other conditions associated with inflammation and impaired gut barrier function.

A sixth aspect of this invention relates to a method of modulating the indigenous microbiota of a non-infant human to increase *Bifidobacterium* abundance and to at least maintain the abundance of *Faecalibacterium*. The method involves administering to the non-infant human a synthetic mixture of HMOs according to the first aspect of this invention or a nutritional or pharmaceutical composition according to the second aspect of this invention, as described above. Increasing the *Bifidobacterium* abundance and at least maintaining the abundance of *Faecalibacterium* render the non-infant human's intestinal milieu less prone to inflammation and provide improved intestinal barrier function. Preferably the abundance of *Ruminococcus gnavus* is reduced. These effects can prevent and/or treat conditions such as inflammatory bowel disease, irritable bowel syndrome, and other conditions associated with inflammation and impaired gut barrier function.

In both the fifth and sixth aspects of the invention, the abundance of Proteobacteria is also preferably reduced.

A seventh aspect of this invention relates to a method of preventing or treating viral and/or bacterial infections in a non-infant human, especially intestinal infections and infections of the respiratory tract. The method comprises administering, to the non-infant human, a synthetic mixture of HMOs according to the first aspect of this invention or a nutritional or pharmaceutical composition according to the second aspect of this invention, as described above.

An eighth aspect of this invention relates to a method of improving the cognitive function of a non-infant human. The method comprises administering, to the non-infant human, a synthetic mixture of HMOs according to the first aspect of this invention or a nutritional or pharmaceutical composition according to the second aspect of this invention, as described above.

DETAILED DESCRIPTION OF THE INVENTION

In accordance with this invention, the following terms preferably have the following meanings:

"Non-infant human" or "non-infant" preferably means a human of 3 years of age and older. Accordingly, a non-infant human is a human of any age above 3 years old, e.g. it can be a child, a teenager, an adult or an elderly person.

"Synthetic mixture of HMOs" means a mixture which is artificially prepared and preferably means a mixture in which at least one HMO is produced ex vivo chemically and/or biologically, e.g. by means of chemical reaction, enzymatic reaction or recombinantly. More preferably, all of the HMOs in the mixture are produced ex vivo chemically and/or biologically. In some embodiments, a synthetic mixture of the invention may be, but preferably is not, identical with a naturally occurring mixture "Microbiota", "microflora" and "microbiome" mean a community of living microorganisms that typically inhabits a bodily organ or part, particularly the gastro-intestinal organs of non-infant humans. The most dominant members of the gastrointestinal microbiota include microorganisms of the phyla of *Firmicutes, Bacteroidetes, Actinobacteria, Proteobacteria, Synergistetes, Verrucomicrobia, Fusobacteria,* and *Euryarchaeota*; at genus level *Bacteroides, Faecalibacterium, Bifidobacterium, Roseburia, Alistipes, Collinsella, Blautia, Coprococcus, Ruminococcus, Eubacterium* and *Dorea*; at species level *Bacteroides uniformis, Alistipes putredinis, Parabacteroides merdae, Ruminococcus bromii, Dorea longicatena, Bacteroides caccae, Bacteroides thetaiotaomicron, Eubacterium hallii, Ruminococcus torques, Faecalibacterium prausnitzii, Ruminococcus lactaris, Collinsella aerofaciens, Dorea form/cigenerans, Bacteroides vulgatus* and *Roseburia intestinalis*. The gastrointestinal microbiota includes the mucosa-associated microbiota, which is located in or attached to the mucus layer covering the epithelium of the gastrointestinal tract, and luminal-associated microbiota, which is found in the lumen of the gastrointestinal tract.

"Modulating of microbiota" means exerting a modifying or controlling influence on microbiota, in particular an influence leading to an increase in the indigenous intestinal abundance of *Bifidobacterium, Barnesiella* and/or *Faecalibacterium*, and reduction of the intestinal abundance of *Ruminococcus gnavus* and/or Proteobacteria.

"Proteobacteria" are a phylum of Gram-negative bacteria and include a wide variety of pathogenic bacteria, such as *Escherichia, Salmonella, Vibrio, Helicobacter, Yersinia* and many other notable genera.

"Therapy" means treatment given or action taken to reduce or eliminate symptoms of a disease or pathological condition.

"Preventive treatment" or "prevention" in the present context means a treatment given or an action taken to diminish the risk of the onset or recurrence of a disease.

"Viral infection" in the present context means an infection of the stomach and intestines, or any other parts of the gastro-intestinal tract, by a virus often resulting in inflammatory response, commonly known as the stomach flu. The symptoms may include one or more of the following: watery diarrhoea, nausea and vomiting, headache, muscle aches, joint aches fever, chills, sweating, clammy skin, abdominal cramps and pain, loss of appetite, weight loss. Examples of viral gastroinfections include, but not limited to, viral gastroinfections caused by Rotavirus or Norovirus.

"Bacterial infection" in the present context means an infection of the stomach and intestines, or any other parts of the gastro-intestinal tract, by a pathogenic bacteria, commonly known as bacterial entheritis. The symptoms may include one or more of the following: loss of appetite, nausea and vomiting, diarrhoea, abdominal pains and cramps, blood in the stool, fever. Examples of bacterial infections include, but not limited to, gastroinfections by pathogenic strains of *Yersinia, Staphylococcus, Shigella, Salmonella, Campylobacter* and *E. coli*.

"Infections of the respiratory tract" refers to any viral and/or bacterial infections of upper and lower respiratory tract, i.e. infections of the sinuses, throat, airways or lungs.

"Cancer" preferably refers to a neoplasm; for example of any part of one or more of the following: respiratory, gastro-intestinal, urinary tracts or liver.

"Oral administration" means any conventional form for the delivery of a composition through the mouth. Accordingly, oral administration is a form of enteral administration.

"Cognitive function" refers to cerebral activities that lead to knowledge, including all means and mechanisms of acquiring information. Cognitive functions encompass reasoning, memory, attention, and language and lead directly to the attainment of information and, thus, knowledge.

In accordance with this invention, it has been surprisingly discovered that a synthetic HMO mixture consisting essentially of LNnT, LNT, 2'-FL, 3'-SL, 6'-SL and either DFL or 3-FL, preferably DFL, and optionally lactose, can provide an anti-infective composition for preventing or treating, bacterial or viral infections through specific modulation of the intestinal microbiota, binding of viruses, reduction in pathogenic translocation and improvement of intestinal barrier function in a non-infant human. Further, the HMO mixture of this invention acts as a decoy receptor and binds to rotaviruses to prevent the rotaviruses from adhering to human intestinal cells. These properties, coupled with an improvement in intestinal barrier function, make the HMO mixture suitable for preventing and treating intestinal infections.

It has also been found that the HMO mixture of this invention can increase the brain ganglioside and glycoprotein sialic acid concentrations, and enhance hippocampal long term potentiation through the vagus nerve, leading to increased synaptogenesis and neurodevelopment in a non-infant human. This makes the HMO mixture suitable for administration to non-infant humans to improve their cognitive function.

The HMO mixture of this invention can also:
i) increase the indigenous intestinal abundance of *Bifidobacterium*, and
ii) increase the intestinal abundance of *Barnesiella* and/or at least maintain the intestinal abundance of *Faecalibacterium*, and
iii) reduce the intestinal abundance of *Ruminococcus gnavus* and/or Proteobacteria
in non-infant humans.

These effects can render an intestinal milieu less prone to inflammation. Coupled with an improvement in intestinal barrier function, these effects of the HMO mixture can prevent and/or treat conditions such as inflammatory bowel disease, irritable bowel syndrome, and other conditions associated with inflammation and impaired barrier function.

Surprisingly, the increase of bifidobacteria in the gut, induced by the HMO mixture of this invention, increases the efficacy of anticancer agents against tumors. The bifidobacteria act as immune helpers, strengthening a cancer patient's response to an anticancer agent. This property makes the HMO mixture suitable as an aid in cancer therapy.

Preferably the HMO mixture of this invention contains: i) about 55 wt % to about 75 wt % of 2'-FL, more preferably about 60 wt % to about 70 wt %; ii) about 2 wt % to about 10 wt % of LNnT, more preferably about 3 wt % to about 7 wt %; iii) about 10 wt % to about 20 wt of LNT, more preferably about 12 wt % to about 18 wt %; iv) about 1 wt % to about 15 wt % of DFL or 3-FL, preferably about 1 wt % to about 10 wt %, even more preferably about 2 wt % to about 10 wt %; v) about 1 wt % to about 10 wt % of 3'-SL, more preferably about 2 wt % to about 8 wt %; and vi) about 1 wt % to about 15 wt % of 6'-SL, preferably about 5 wt % to about 15 wt %, more preferably about 7 wt % to about 13 wt %. The HMO mixture of this invention can also contain lactose, but it is not considered an active ingredient of the mixture.

The synthetic HMO mixture can be administered to a non-infant human in any suitable form such as a nutritional or pharmaceutical composition, for example, a unit dosage form (for example, a tablet, a capsule, a sachet of powder, etc.).

The nutritional or pharmaceutical composition consists of the synthetic mixture of HMOs consisting essentially of LNnT, LNT, 2'-FL, 3'-SL, 6'-SL, either DFL or 3-FL, and optionally lactose, and suitable excipients. The nutritional or pharmaceutical composition does not contain any other HMOs than those mentioned above.

In one embodiment, the HMO mixture of this invention can be in the form of a nutritional composition. For example, the nutritional composition can be a food composition, a rehydration solution, or a dietary maintenance or supplement for elderly individuals or immunocompromised individuals. The nutritional composition can contain sources of protein, lipids and/or digestible carbohydrates and can be in powdered or liquid forms. The composition can be designed to be the sole source of nutrition or a nutritional supplement.

Suitable protein sources include milk proteins, soy protein, rice protein, pea protein and oat protein, or mixtures thereof. Milk proteins can be in the form of milk protein concentrates, milk protein isolates, whey protein or casein, or mixtures of both. The protein can be whole protein or hydrolysed protein, either partially hydrolysed or extensively hydrolysed. Hydrolysed protein offers the advantage of easier digestion which can be important for non-infants with inflamed GI tracts. The protein can also be provided in the form of free amino acids. The protein can comprise about 5% to about 30% of the energy of the nutritional composition, normally about 10% to 20%.

The protein source can be a source of glutamine, threonine, cysteine, serine, proline, or a combination of these amino acids. The glutamine source can be a glutamine dipeptide and/or a glutamine enriched protein. Glutamine can be included due to the use of glutamine by enterocytes as an energy source. Threonine, serine and proline are important amino acids for the production of mucin. Mucin coats the GI tract and can improve mucosal healing. Cysteine is a major precursor of glutathione, which is key for the antioxidant defences of the body.

Suitable digestible carbohydrates include maltodextrin, hydrolysed or modified starch or corn starch, glucose polymers, corn syrup, corn syrup solids, high fructose corn syrup, rice-derived carbohydrates, pea-derived carbohydrates, potato-derived carbohydrates, tapioca, sucrose, glucose, fructose, sucrose, lactose, honey, sugar alcohols (e.g., maltitol, erythritol, sorbitol), or mixtures thereof. Preferably the composition is free from added lactose. Generally digestible carbohydrates provide about 35% to about 55% of the energy of the nutritional composition. A particularly suitable digestible carbohydrate is a low dextrose equivalent (DE) maltodextrin.

Suitable lipids include medium chain triglycerides (MCT) and long chain triglycerides (LCT). Preferably the lipid is a mixture of MCTs and LCTs. For example, MCTs can comprise about 30% to about 70% by weight of the lipids, more specifically about about 50% to about 60% by weight. MCTs offer the advantage of easier digestion which can be important for non-infants with inflamed GI tracts. Generally, the lipids provide about 35% to about 50% of the energy of the nutritional composition. The lipids can contain essential fatty acids (omega-3 and omega-6 fatty acids). Preferably these polyunsaturated fatty acids provide less than about 30% of total energy of the lipid source. Decreasing the levels of these polyunsaturated fatty acids is believed to decrease sensitivity to peroxidation; which can be beneficial for non-infants having inflammatory conditions.

Suitable sources of long chain triglycerides are rapeseed oil, sunflower seed oil, palm oil, soy oil, milk fat, corn oil, high oleic oils, and soy lecithin. Fractionated coconut oils are a suitable source of medium chain triglycerides. The lipid profile of the nutritional composition is preferably designed to have a polyunsaturated fatty acid omega-6 (n-6) to omega-3 (n-3) ratio of about 4:1 to about 10:1. For example, the n-6 to n-3 fatty acid ratio can be about 6:1 to about 9:1.

The nutritional composition may also include vitamins and minerals. If the nutritional composition is intended to be a sole source of nutrition, it preferably includes a complete vitamin and mineral profile. Examples of vitamins include vitamins A, B-complex (such as B1, B2, B6 and B12), C, D, E and K, niacin and acid vitamins such as pantothenic acid, folic acid and biotin. Examples of minerals include calcium, iron, zinc, magnesium, iodine, copper, phosphorus, manganese, potassium, chromium, molybdenum, selenium, nickel, tin, silicon, vanadium and boron.

The nutritional composition can also include a carotenoid such as lutein, lycopene, zeaxanthin, and beta-carotene. The total amount of carotenoid included can vary from about 0.001 μg/ml to about 10 μg/ml. Lutein can be included in an amount of from about 0.001 μg/ml to about 10 μg/ml, preferably from about 0.044 μg/ml to about 5 μg/ml of lutein. Lycopene can be included in an amount from about 0.001 μg/ml to about 10 μg/ml, preferably about 0.0185 μg/ml to about 5 μg/ml of lycopene. Beta-carotene can comprise from about 0.001 μg/ml to about 10 mg/ml, for example about 0.034 μg/ml to about 5 μg/ml of beta-carotene.

The nutritional composition preferably also contains reduced concentrations of sodium; for example, from about 300 mg/l to about 400 mg/l. The remaining electrolytes can be present in concentrations set to meet needs without providing an undue renal solute burden on kidney function. For example, potassium is preferably present in a range of about 1180 to about 1300 mg/l; and chloride is preferably present in a range of about 680 to about 800 mg/l.

The nutritional composition can also contain various other conventional ingredients such as preservatives, emulsifying agents, thickening agents, buffers, fibres and prebiotics (e.g. fructooligosaccharides, galactooligosaccharides), probiotics (e.g. *B. animalis* subsp. lactis BB-12, *B. lactis* HNO19, *B. lactis* Bi07, *B. infantis* ATCC 15697, *L. rhamnosus* GG, *L. rhamnosus* HNOOI, *L. acidophilus* LA-5, *L. acidophilus* NCFM, *L. fermentum* CECT5716, *B. longum* BB536, *B. longum* AH1205, *B. longum* AH1206, *B. breve* M-16V, *L. reuteri* ATCC 55730, *L. reuteri* ATCC PTA-6485, *L. reuteri* DSM 17938), antioxidant/anti-inflammatory compounds including tocopherols, caroteinoids, ascorbate/vitamin C, ascorbyl palmitate, polyphenols, glutathione, and superoxide dismutase (melon), other bioactive factors (e.g. growth hormones, cytokines, TFG-β), colorants, flavours, and stabilisers, lubricants, and so forth.

The nutritional composition can be formulated as a soluble powder, a liquid concentrate, or a ready-to-use formulation. The composition can be fed to a human in need via a nasogastric tube or orally. Various flavours, fibres and other additives can also be present.

The nutritional compositions can be prepared by any commonly used manufacturing techniques for preparing nutritional compositions in solid or liquid form. For example, the composition can be prepared by combining various feed solutions. A protein-in-fat feed solution can be prepared by heating and mixing the lipid source and then adding an emulsifier (e.g. lecithin), fat soluble vitamins, and at least a portion of the protein source while heating and stirring. A carbohydrate feed solution is then prepared by adding minerals, trace and ultra trace minerals, thickening or suspending agents to water while heating and stirring. The resulting solution is held for 10 minutes with continued heat and agitation before adding carbohydrates (e.g. the HMOs and digestible carbohydrate sources). The resulting feed solutions are then blended together while heating and agitating and the pH adjusted to 6.6-7.0, after which the composition is subjected to high-temperature short-time processing during which the composition is heat treated, emulsified and homogenized, and then allowed to cool. Water soluble vitamins and ascorbic acid are added, the pH is adjusted to the desired range if necessary, flavours are added, and water is added to achieve the desired total solid level.

For a liquid product, the resulting solution can then be aseptically packed to form an aseptically packaged nutritional composition. In this form, the nutritional composition can be in ready-to-feed or concentrated liquid form. Alternatively, the composition can be spray-dried and processed and packaged as a reconstitutable powder.

When the nutritional product is a ready-to-feed nutritional liquid, it may be preferred that the total concentration of HMOs in the liquid, by weight of the liquid, is from about 0.0001% to about 2.0%, including from about 0.001% to about 1.5%, including from about 0.01% to about 1.0%. When the nutritional product is a concentrated nutritional liquid, it may be preferred that the total concentration of HMOs in the liquid, by weight of the liquid, is from about 0.0002% to about 4.0%, including from about 0.002% to about 3.0%, including from about 0.02% to about 2.0%.

In other embodiment, the HMO mixture of this invention can be comprised in a pharmaceutical composition. The pharmaceutical composition can contain a pharmaceutically acceptable carrier, e.g. phosphate buffered saline solution, mixtures of ethanol in water, water and emulsions such as an oil/water or water/oil emulsion, as well as various wetting agents or excipients. The pharmaceutical composition can also contain other materials that do not produce an adverse, allergic or otherwise unwanted reaction when administered to non-infants. The carriers and other materials can include solvents, dispersants, coatings, absorption promoting agents, controlled release agents, and one or more inert excipients, such as starches, polyols, granulating agents, microcrystalline cellulose, diluents, lubricants, binders, and disintegrating agents. If desired, tablet dosages of the anti-infective compositions can be coated by standard aqueous or non-aqueous techniques.

The pharmaceutical compositions can be administered orally, e.g. as a tablet, capsule, or pellet containing a predetermined amount, or as a powder or granules containing a predetermined concentration or a gel, paste, solution, suspension, emulsion, syrup, bolus, electuary, or slurry, in an aqueous or non-aqueous liquid, containing a predetermined concentration. Orally administered compositions can include binders, lubricants, inert diluents, flavouring agents, and humectants. Orally administered compositions such as tablets can optionally be coated and can be formulated so as to provide sustained, delayed or controlled release of the mixture therein.

The pharmaceutical compositions can also be administered by rectal suppository, aerosol tube, naso-gastric tube or direct infusion into the GI tract or stomach.

The pharmaceutical compositions can also include therapeutic agents such as antiviral agents, antibiotics, probiotics, analgesics, and anti-inflammatory agents. The proper dosage of these compositions for a non-infant human can be determined in a conventional manner, based upon factors such immune status, body weight and age. In some cases, the dosage will be at a concentration similar to that found for the HMOs in human breast milk. The required amount would generally be in the range from about 200 mg to about 20 g per day, in certain embodiments from about 300 mg to about 15 g per day, from about 400 mg to about 10 g per day, in certain embodiments from about 500 mg to about 10 g per day, in certain embodiments from about 1 g to about 10 g per day. Appropriate dose regimes can be determined by conventional methods.

Pharmaceutical compositions of the invention can be used for treatment of a concerned disease in combination with other medicaments prescribed for said disease, e.g. in combination with an anti-diabetes medicine or antibiotic therapy.

Yet in other embodiment, the composition comprising the HMO mixture of this invention is a unit dosage form. The unit dosage form can contain an acceptable carrier, e.g. phosphate buffered saline solution, mixtures of ethanol in water, water and emulsions such as an oil/water or water/oil emulsion, as well as various wetting agents or excipients. The unit dosage form can also contain other materials that do not produce an adverse, allergic or otherwise unwanted reaction when administered to a patient. The carriers and other materials can include solvents, dispersants, coatings, absorption promoting agents, controlled release agents, and one or more inert excipients, such as starches, polyols, granulating agents, microcrystalline cellulose, diluents, lubricants, binders, and disintegrating agents. If desired, tablet dosages of the composition can be coated by standard aqueous or nonaqueous techniques.

A unit dosage form of this invention can be administered orally, e.g. as a tablet, capsule, or pellet containing a predetermined amount of the mixture, or as a powder or granules containing a predetermined concentration of the mixture or a gel, paste, solution, suspension, emulsion, syrup, bolus, electuary, or slurry, in an aqueous or nonaqueous liquid, containing a predetermined concentration of the mixture. An orally administered composition can include one or more binders, lubricants, inert diluents, flavouring agents, and humectants. An orally administered composition such as a tablet can optionally be coated and can be formulated so as to provide sustained, delayed or controlled release of the HMO mixture therein.

A unit dosage form of this invention can also be administered by rectal suppository, aerosol tube, naso-gastric tube or direct infusion into the GI tract or stomach.

A unit dosage form of this invention can also include therapeutic agents such as antiviral agents, antibiotics, probiotics, analgesics, and anti-inflammatory agents. The proper dosage of such a composition for a patient can be determined in a conventional manner, based upon factors such as the patient's immune status, body weight and age. In some cases, the dosage will be at a concentration similar to that found for the HMOs of the composition in human breast milk. The required amount would generally be in the range from about 200 mg to about 20 g per day, in certain embodiments from about 300 mg to about 15 g per day, from about 400 mg to about 10 g per day, in certain embodiments from about 500 mg to about 10 g per day, in certain embodiments from about 1 g to about 10 g per day. Appropriate dose regimes can be determined by methods known to those skilled in the art.

EXAMPLES

Example 1

A total of 50 healthy male and female subjects are recruited to participate in the study. After a screening visit and run-in period of 1-2 weeks, the subjects are selected and randomized into 2 groups, each of 25 subjects. One group is administered a treatment product containing 5 g of the following HMO mixture of this invention:
  i) 14.2 wt % of LNT
  ii) 5.3 wt % of LNnT
  iii) 63.7 wt % of 2'-FL
  iv) 4.2 wt % of DFL,
  v) 3.7 wt % of 3'-SL and
  vi) 8.9 wt % of 6'-SL The other group is administered a placebo (containing 2 grams of glucose). The treatment product and the placebo are in powder form in a unit dosage container.

The subjects are eligible to participate if they are at least 18 years of age. All recruited subjects are able and willing to understand and comply with the study procedures. Subjects are excluded if: they have participated in a clinical study one month prior to screening visit; they have abnormal results in the screening tests which are clinically relevant for study participation; they are suffering for a severe disease such as malignancy, diabetes, severe coronary disease, kidney disease, neurological disease, or severe psychiatric disease or any condition which can confound the results of the study; used highly dosed probiotic supplements (yoghurt allowed) for 3 months prior to the study; consumed antibiotic drugs 3 months prior to the study; consumed on a regular basis any medication that might interfere with symptom evaluation 2 weeks prior to the study; and pregnant or lactating.

At the screening visit, medical history and concomitant medication is registered and a blood sample for safety analyses is collected. A faecal sample kit is distributed. Subjects are instructed to keep their samples in the freezer until the next visit.

At the second visit, eligibility criteria are checked and eligible subjects are randomised to the two arms in the trial. The faecal samples are collected and equipment for new samples are distributed. Subjects are familiarised with an interactive internet enabled system which records data daily and are provided with either treatment or placebo products. Subjects are reminded not to change their usual diet during the study. Blood samples are collected for biomarker studies. The faecal samples are stored at −80° C. until analysis. Faecal samples are subjected to 16S rRNA sequencing analysis.

The study runs for 8 weeks with the subjects consuming either a placebo or a treatment product daily. Subjects are instructed to consume the products in the morning with breakfast. Compliance is monitored through the interactive internet enabled system. The subjects also use the system to record:
- Bristol Stool Form (BSF) scale information,
- symptom information such as abdominal pain, abdominal discomfort, abdominal cramping, abdominal bloating, and abdominal fullness,
- additional Gastrointestinal Symptom Rating Scale (GSRS) information.

This questionnaire includes 15 items covering five dimensions (abdominal pain, indigestion, reflux, diarrhoea, constipation) and uses a seven-graded Likert scale.

At the end of the study, each subject has an exit visit with the medical team. Faecal samples and blood samples are collected and analysed as before.

The faecal analysis indicates that the subjects treated with the HMO mixture of this invention have increased abundance of *Bifidobacterium* and *Barnesiella* and reduced abundance of Firmicutes, especially *Clostridia*, and *Ruminococcus gnavus*. The abundance of *Faecalibacterium* is unchanged in these subjects. The abundance of Proteobacteria is decreased in these subjects.

Example 2

A total of 50 healthy male and female subjects are recruited to participate in the study. After a screening visit and run-in period of 1-2 weeks, the subjects are selected and randomized into 2 groups, each of 25 subjects. One group is administered a treatment product containing 5 g of the following HMO mixture of this invention:
- i) 14.2 wt % of LNT
- ii) 5.3 wt % of LNnT
- iii) 63.7 wt % of 2'-FL
- iv) 4.2 wt % of 3-FL,
- v) 3.7 wt % of 3'-SL and
- vi) 8.9 wt % of 6'-SL The other group is administered a placebo (containing 2 grams of glucose). The treatment product and the placebo are in powder form in a unit dosage container.

The subjects are eligible to participate if they are at least 18 years of age. All recruited subjects are able and willing to understand and comply with the study procedures. Subjects are excluded if: they have participated in a clinical study one month prior to screening visit; they have abnormal results in the screening tests which are clinically relevant for study participation; they are suffering for a severe disease such as malignancy, diabetes, severe coronary disease, kidney disease, neurological disease, or severe psychiatric disease or any condition which can confound the results of the study; used highly dosed probiotic supplements (yoghurt allowed) for 3 months prior to the study; consumed antibiotic drugs 3 months prior to the study; consumed on a regular basis any medication that might interfere with symptom evaluation 2 weeks prior to the study; and pregnant or lactating.

At the screening visit, medical history and concomitant medication is registered and a blood sample for safety analyses is collected. A faecal sample kit is distributed. Subjects are instructed to keep their samples in the freezer until the next visit.

At the second visit, eligibility criteria are checked and eligible subjects are randomised to the two arms in the trial. The faecal samples are collected and equipment for new samples are distributed. Subjects are familiarised with an interactive internet enabled system which records data daily and are provided with either treatment or control products. Subjects are reminded not to change their usual diet during the study. Blood samples are collected for biomarker studies. The faecal samples are stored at −80° C. until analysis. Faecal samples are subjected to 16S rRNA sequencing analysis.

The study runs for 8 weeks with the subjects consuming either a placebo or a treatment product daily. Subjects are instructed to consume the products in the morning with breakfast. Compliance is monitored through the interactive internet enabled system. The subjects also use the system to record:
- Bristol Stool Form (BSF) scale information,
- symptom information such as abdominal pain, abdominal discomfort, abdominal cramping, abdominal bloating, and abdominal fullness,
- additional Gastrointestinal Symptom Rating Scale (GSRS) information.

This questionnaire includes 15 items covering five dimensions (abdominal pain, indigestion, reflux, diarrhoea, constipation) and uses a seven-graded Likert scale.

At the end of the study, each subject has an exit visit with the medical team. Faecal samples and blood samples are collected and analysed as before.

The faecal analysis indicates that the subjects treated with the HMO mixture of this invention have increased abundance of *Bifidobacterium* and *Barnesiella* and reduced abundance of Firmicutes, especially *Clostridia*, and *Ruminococcus gnavus*. The abundance of *Faecalibacterium* is unchanged in these subjects. The abundance of Proteobacteria is decreased in these subjects.

Example 3

Twenty 7-week-old C57BL/6J female mice are individually housed to avoid contamination between mice and provided with irradiated food and water. The mice are separated into 2 groups, each of 10 mice.

The mice are treated with ampicillin (0.5 g/liter) in their drinking water, which is changed every 3 days. After 1 week, the ampicillin addition to the drinking water is terminated. Thereafter, 1 group is administered a treatment product containing the following HMO mixture of this invention:
- 14.2 wt % of LNT
- 5.3 wt % of LNnT
- 63.7 wt % of 2'-FL
- 4.2 wt % of DFL,
- 3.7 wt % of 3'-SL and
- 8.9 wt % of 6'-SL.

The treatment product is added to the drinking water of 1 group at a total concentration of 40 mg/ml. The other group receives drinking water with 40 mg/ml of glucose. Fresh water is administered daily, and all mice have free access to the drinking water. The mice are fed a rodent chow and are given fresh chow daily.

Two days after termination of the ampicillin treatment, mice of each group are infected by oral gavage with a vancomycin-resistant *Enterococcus faecium* strain (VRE). Fresh faecal pellets are collected at different time points to determine the VRE levels. VRE is quantified by plating serial dilutions of faecal pellets on Enterococcosel agar plates with vancomycin. VRE colonies are identified by appearance and confirmed by Gram staining. PCR of the vanA gene, which confers resistance to vancomycin, is used to confirm the presence of VRE in infected mice.

The mice are monitored for 2 weeks and are then euthanized. Luminal contents from the ilium, cecum and colon are collected and immediately frozen and stored at −80° C. DNA is extracted using a 96-well PowerSoil DNA Isolation Kit (MO-BIO). A minimum of one sample-well per plate is kept empty to serve as a negative control during PCR. PCR is done with the forward primer S-D-Bact-0341-b-S-17 and reverse primer S-D-Bact-0785-a-A-21 (Klindworth et al. *Nucleic Acids Res.* 41, el (2013)) with Illumina adapters attached. These are universal bacterial 16S rDNA primers, which target the V3-V4 region. The following PCR program is used: 98° C. for 30 sec, 25× (98° C. for 10 s, 55° C. for 20 s, 72° C. for 20 s), 72° C. for 5 min. Amplification is verified by running the products on a 1% agarose gel. Barcodes are added in a nested PCR using the Nextera Index Kit V2 (Illumina) with the following PCR program: 98° C. for 30 sec, 8× (98° C. for 10 s, 55° C. for 20 s, 72° C. for 20 s), 72° C. for 5 min. Attachment of primers is verified by running the products on a 1% agarose gel.

Products from the nested PCR are normalized using the SequalPrep Normalization Plate Kit and pooled. Pooled libraries are concentrated by evaporation and the DNA concentration of pooled libraries wisas measured on a Qubit fluorometer using the Qubit High Sensitivity Assay Kit (Thermo Fisher Scientific). Sequencing is done on a MiSeq desktop sequencer using the MiSeq Reagent Kit V3 (Illumina) for 2×300 bp paired-end sequencing. The 64-bit version of USEARCH (Edgar, 2013) is used for bioinformatical analysis of the sequence data.

In the mice treated with the HMO mixture of this invention, VRE colonisation is reduced to undetectable levels within 14 days. The density of VRE reduces within 5 days. The mice treated with the HMO mixture also showed a higher abundance of Porphyromonadaceae, especially *Barnesiella*. The untreated mice continue to harbour large numbers of VRE throughout the intestine.

Example 4

Twenty 7-week-old C57BL/6J female mice are individually housed to avoid contamination between mice and provided with irradiated food and water. The mice are separated into 2 groups, each of 10 mice.

The mice are treated with ampicillin (0.5 g/liter) in their drinking water, which is changed every 3 days. After 1 week, the ampicillin addition to the drinking water is terminated. Thereafter, 1 group is administered a treatment product containing the following HMO mixture of this invention:
 14.2 wt % of LNT
 5.3 wt % of LNnT
 63.7 wt % of 2'-FL
 4.2 wt % of 3-FL,
 3.7 wt % of 3'-SL and
 8.9 wt % of 6'-SL.

The treatment product is added to the drinking water of 1 group at a total concentration of 40 mg/ml. The other group receives drinking water with 40 mg/ml of glucose. Fresh water is administered daily, and all mice have free access to the drinking water. The mice are fed a rodent chow and are given fresh chow daily.

Two days after termination of the ampicillin treatment, mice of each group are infected by oral gavage with a vancomycin-resistant *Enterococcus faecium* strain (VRE). Fresh faecal pellets are collected at different time points to determine the VRE levels. VRE is quantified by plating serial dilutions of faecal pellets on Enterococcosel agar plates with vancomycin. VRE colonies are identified by appearance and confirmed by Gram staining. PCR of the vanA gene, which confers resistance to vancomycin, is used to confirm the presence of VRE in infected mice.

The mice are monitored for 2 weeks and are then euthanized. Luminal contents from the ilium, cecum and colon are collected and immediately frozen and stored at −80° C. DNA is extracted using a 96-well PowerSoil DNA Isolation Kit (MO-BIO). A minimum of one sample-well per plate is kept empty to serve as a negative control during PCR. PCR is done with the forward primer S-D-Bact-0341-b-S-17 and reverse primer S-D-Bact-0785-a-A-21 (Klindworth et al. *Nucleic Acids Res.* 41, el (2013)) with Illumina adapters attached. These are universal bacterial 16S rDNA primers, which target the V3-V4 region. The following PCR program is used: 98° C. for 30 sec, 25× (98° C. for 10 s, 55° C. for 20 s, 72° C. for 20 s), 72° C. for 5 min. Amplification is verified by running the products on a 1% agarose gel. Barcodes are added in a nested PCR using the Nextera Index Kit V2 (Illumina) with the following PCR program: 98° C. for 30 sec, 8× (98° C. for 10 s, 55° C. for 20 s, 72° C. for 20 s), 72° C. for 5 min. Attachment of primers is verified by running the products on a 1% agarose gel.

Products from the nested PCR are normalized using the SequalPrep Normalization Plate Kit and pooled. Pooled libraries are concentrated by evaporation and the DNA concentration of pooled libraries wisas measured on a Qubit fluorometer using the Qubit High Sensitivity Assay Kit (Thermo Fisher Scientific). Sequencing is done on a MiSeq desktop sequencer using the MiSeq Reagent Kit V3 (Illumina) for 2×300 bp paired-end sequencing. The 64-bit version of USEARCH (Edgar, 2013) is used for bioinformatical analysis of the sequence data.

In the mice treated with the HMO mixture of this invention, VRE colonisation is reduced to undetectable levels within 14 days. The density of VRE reduces within 5 days. The mice treated with the HMO mixture also showed a higher abundance of Porphyromonadaceae, especially *Barnesiella*. The untreated mice continue to harbour large numbers of VRE throughout the intestine.

Example 5

Forty-five 6-week-old female C57BL/6 mice are injected subcutaneously with B16 melanoma cells. The mice are then randomly assigned to three groups (fifteen mice in each group), and individually housed to avoid contamination between mice. The mice are fed a pelleted semi-synthetic AIN 76 diet (Research Diets Inc., New Brunswick, NJ) with:
 5% of the following HMO mixture of this invention in the feed for group A:
  14.2 wt % of LNT
  5.3 wt % of LNnT
  63.7 wt % of 2'-FL
  4.2 wt % of DFL,
  3.7 wt % of 3'-SL and
  8.9 wt % of 6'-SL;
 5% of the following HMO mixture of this invention in the feed for group B:
  14.2 wt % of LNT
  5.3 wt % of LNnT 63.7 wt % of 2'-FL
4.2 wt % of 3-FL,
3.7 wt % of 3'-SL and
8.9 wt % of 6'-SL; and
5% corn-starch in the feed for group C (control).

Fresh water is administered daily and all mice have free access to drinking water and feed. Three days after the tumor implantation, mice are injected with 200 μg of CTLA-4 antibodies. Additional antibody treatments are given every 3 days until the end of the experiment (14 days). Food consumption, bodyweight and tumor volume (diameter) are measured throughout the study. Fresh faecal samples are collected at day 0, 4, 7, 10, and 14. Samples are immediately frozen and stored at −80° C. until further analysis.

Fourteen days after implantation of the B16 cells, mice are euthanized by cervical dislocation. Tumors are excised and weighed. Sections of tumors are fixed in 4% paraformaldehyde and stored at −80° C. Mucosal and intestinal contents from caecum and colon are removed and stored at −80° C.

For analysis of tumor infiltrating T cells, tumors are minced into small pieces and digested with 0.2 mg/ml DNase and 1.67 Wünsch U/ml Liberase (Roche). Obtained cell suspensions are filtered through a 40-μm nylon cell strainer and red blood cells lysed. $CD8^+$ T cells are purified from B16 tumor-derived cell suspensions using CD8α (Ly-2) MicroBeads (Miltenyi Biotec), following the manufacturer's protocol. Obtained cells are incubated for 2 hours in the presence of 1 μl/ml of brefeldin A, washed and incubated with rat anti-mouse CD16/CD32 mAb (2.4G2) to block nonspecific binding, and then stained with CD8α-PE-Cy5 and CD69-PE, followed by intracellular staining with IFN-γ-PE-Cy7 or isotype control antibodies according to the manufacturer's instructions (BD Bioscience-Pharmingen). The density of $CD8\ GFP^+$ and $GFP^-$ T cells in the tumors are calculated by dividing the total number of obtained cells by the tumor weight.

To assess the microbiota profile, DNA is extracted from the faecal samples, mucosal and intestinal content using a 96-well PowerSoil DNA Isolation Kit (MO-BIO). A minimum of one sample-well per plate is kept empty to serve as a negative control during PCR. PCR is done with the forward primer S-D-Bact-0341-b-S-17 and reverse primer S-D-Bact-0785-a-A-21 (Klindworth et al. Nucleic Acids Res. 41, el (2013)) with Illumina adapters attached. These are universal bacterial 16S rDNA primers, which target the V3-V4 region. The following PCR program is used: 98° C. for 30 sec, 25× (98° C. for 10 s, 55° C. for 20 s, 72° C. for 20 s), 72° C. for 5 min. Amplification is verified by running the products on a 1% agarose gel. Barcodes are added in a nested PCR using the Nextera Index Kit V2 (Illumina) with the following PCR program: 98° C. for 30 sec, 8× (98° C. for 10 s, 55° C. for 20 s, 72° C. for 20 s), 72° C. for 5 min. Attachment of primers is verified by running the products on a 1% agarose gel. Products from the nested PCR are normalized using the SequalPrep Normalization Plate Kit and pooled. Pooled libraries are concentrated by evaporation and the DNA concentration of pooled libraries is measured on a Qubit fluorometer using the Qubit High Sensitivity Assay Kit (Thermo Fisher Scientific). Sequencing is done on a MiSeq desktop sequencer using the MiSeq Reagent Kit V3 (Illumina) for 2×300 bp paired-end sequencing. The 64-bit version of USEARCH (Edgar, 2013) is used for bioinformatical analysis of the sequence data.

The results show that ingestion of both HMO mixtures beneficially modulates the microbiota by increasing the abundance of bifidobacteria both in the mucosal and luminal intestinal environment. Additionally, the results show that the abundance of bifidobacteria positively correlates with the priming and accumulation of infiltrating T cells in the tumor microenvironment and negatively correlates with tumor size. Collectively, these results indicate that both HMO mixtures can increase the abundance of bifidobacteria and through this increase the efficacy of anti-cancer agents against tumor outgrowth.

Example 6

Mice (5 weeks old; n=30) are randomly allocated to one of the following groups: A) control (n=10); B) 1% mixture of HMOs (n=10); C) 5% mixture of HMOs (n=10). The composition of the HMO blend is given in the table below.

|  | g/100 ml | |
| --- | --- | --- |
|  | 1% | 5% |
| 2'-FL (g) | 0.64 | 3.20 |
| LNnT (g) | 0.05 | 0.25 |
| LNT (g) | 0.14 | 0.70 |
| 3'-SL (g) | 0.05 | 0.25 |
| 6'-SL (g) | 0.09 | 0.45 |
| DFL (g) | 0.05 | 0.25 |

The HMOs are provided in drinking water. All animals have free access to same diet (KLIBA 2122).

After 2 weeks, the mice are challenged with Influenza strain PR8 at a dose of 100 PFU per mouse by intranasal inoculation. The mice are monitored for the next 14 days to assess clinical score of illness symptoms and body weight loss.

The results show that the HMO mixture protects against sickness symptoms and body weight loss caused by the influenza virus infection.

The invention claimed is:

1. A method of increasing the abundance of *Bifidobacterium* in a non-infant human in order to increase the efficacy of anticancer agents against tumors in a non-infant human cancer patient, the method comprising:
    administering, to the non-infant human, a synthetic mixture of HMOs consisting essentially of LNnT, LNT, 2'-FL, 3'-SL, 6'-SL, either DFL or 3-FL and, optionally, lactose;
wherein the synthetic mixture is not identical with a naturally occurring mixture.

2. A method of increasing the abundance of *Bifidobacterium* or *Barnesiella* and to reduce the abundance of *Ruminococcus gnavus* in a non-infant human, the method comprising:
    administering, to the non-infant human, a synthetic mixture of HMOs consisting essentially of LNnT, LNT, 2'-FL, 3'-SL, 6'-SL, either DFL or 3-FL and, optionally, lactose;
    wherein the synthetic mixture is not identical with a naturally occurring mixture.

3. A method of increasing *Bifidobacterium* abundance and to at least maintain the abundance of *Faecalibacterium* in a non-infant human, the method comprising:
    administering, to the human, a synthetic mixture of HMOs consisting essentially of LNnT, LNT, 2'-FL, 3'-SL, 6'-SL, either DFL or 3-FL and, optionally, lactose;
    wherein the synthetic mixture is not identical with a naturally occurring mixture.

4. The method of claim 1, wherein the method increases the abundance of *Bifidobacterium* and *Barnesiella*.

5. The method of claim 1, wherein the synthetic mixture of HMOs consists essentially of LNnT, LNT, 2'-FL, 3'-SL, DFL, 6'-SL and lactose.

6. The method of claim 1, wherein the synthetic mixture of HMOs consists essentially of LNnT, LNT, 2'-FL, 3'-SL, 6'-SL and DFL.

7. The method of claim 1, wherein the synthetic mixture consists essentially of:
   i. about 55 wt % to about 75 wt % of 2'-FL;
   ii. about 2 wt % to about 10 wt % of LNnT;
   iii. about 10 wt % to about 20 wt % of LNT;
   iv. about 1 wt % to about 15 wt % of DFL or 3-FL;
   v. about 1 wt % to about 10 wt % 3'-SL; and
   vi. about 1 wt % to about 15 wt % of 6'-SL.

8. The method of claim 7, wherein the synthetic mixture consists essentially of:
   i. about 60 wt % to about 70 wt % of 2'-FL;
   ii. about 3 wt % to about 7 wt % of LNnT;
   iii. about 12 wt % to about 18 wt % of LNT;
   iv. about 2 wt % to about 10 wt %, of DFL or 3-FL;
   v. about 2 wt % to about 8 wt %, of 3'-SL; and
   vi. about 5 wt % to about 15 wt % of 6'-SL.

9. The method of claim 7, wherein the synthetic mixture comprises about 7 wt % to about 13 wt % of 6'-SL.

10. The method of claim 2, wherein the method further reduces the abundance of Proteobacteria.

11. The method of claim 2, wherein the synthetic mixture of HMOs consist essentially of LNnT, LNT, 2'-FL, 3'-SL, DFL, 6'-SL and lactose.

12. The method of claim 2, wherein the synthetic mixture of HMOs consist essentially of LNnT, LNT, 2'-FL, 3'-SL, 6'-SL and DFL.

13. The method of claim 2, wherein the synthetic mixture consists essentially of:
   i. about 55 wt % to about 75 wt % of 2'-FL;
   ii. about 2 wt % to about 10 wt % of LNnT;
   iii. about 10 wt % to about 20 wt % of LNT;
   iv. about 1 wt % to about 15 wt % of DFL or 3-FL;
   v. about 1 wt % to about 10 wt % 3'-SL; and
   vi. about 1 wt % to about 15 wt % of 6'-SL.

14. The method of claim 13, wherein the synthetic mixture consists essentially of:
   i. about 60 wt % to about 70 wt % of 2'-FL;
   ii. about 3 wt % to about 7 wt % of LNnT;
   iii. about 12 wt % to about 18 wt % of LNT;
   iv. about 2 wt % to about 10 wt %, of DFL or 3-FL;
   v. about 2 wt % to about 8 wt %, of 3'-SL; and
   vi. about 5 wt % to about 15 wt % of 6'-SL.

15. The method of claim 13, wherein the synthetic mixture comprises about 7 wt % to about 13 wt % of 6'-SL.

16. The method of claim 3, wherein the method further reduces the abundance of Proteobacteria.

17. The method of claim 3, wherein the synthetic mixture of HMOs consist essentially of LNnT, LNT, 2'-FL, 3'-SL, DFL, 6'-SL and lactose.

18. The method of claim 3, wherein the synthetic mixture of HMOs consist essentially of LNnT, LNT, 2'-FL, 3'-SL, 6'-SL and DFL.

19. The method of claim 3, wherein the synthetic mixture consists essentially of:
   i. about 55 wt % to about 75 wt % of 2'-FL;
   ii. about 2 wt % to about 10 wt % of LNnT;
   iii. about 10 wt % to about 20 wt % of LNT;
   iv. about 1 wt % to about 15 wt % of DFL or 3-FL;
   v. about 1 wt % to about 10 wt % 3'-SL; and
   vi. about 1 wt % to about 15 wt % of 6'-SL.

20. The method of claim 19, wherein the synthetic mixture consists essentially of:
   i. about 60 wt % to about 70 wt % of 2'-FL;
   ii. about 3 wt % to about 7 wt % of LNnT;
   iii. about 12 wt % to about 18 wt % of LNT;
   iv. about 2 wt % to about 10 wt %, of DFL or 3-FL;
   v. about 2 wt % to about 8 wt %, of 3'-SL; and
   vi. about 5 wt % to about 15 wt % of 6'-SL.

\* \* \* \* \*